United States Patent [19]

Picard et al.

[11] Patent Number: 5,214,206

[45] Date of Patent: May 25, 1993

[54] AMINOSULFONYL UREA ACAT INHIBITORS

[75] Inventors: Joseph A. Picard; Drago R. Sliskovic, both of Ypsilanti, Mich.

[73] Assignee: Warner-Lambert Company, Morris Plains, N.J.

[21] Appl. No.: 747,040

[22] Filed: Aug. 19, 1991

Related U.S. Application Data

[63] Continuation-in-part of Ser. No. 610,287, Nov. 7, 1990, abandoned.

[51] Int. Cl.$^5$ .................. A61K 31/175; C07C 311/00
[52] U.S. Cl. ..................... 564/40; 514/231.2; 514/237.8; 514/238.2; 514/247; 514/255; 514/256; 514/307; 514/311; 514/315; 514/357; 514/359; 514/365; 514/373; 514/378; 514/381; 514/383; 514/406; 514/416; 514/419; 514/424; 514/427; 514/438; 514/443; 514/461; 514/469; 514/481; 514/593; 514/824
[58] Field of Search ............... 564/40; 514/593, 824

[56] References Cited

U.S. PATENT DOCUMENTS

| | | | |
|---|---|---|---|
| 2,312,404 | 3/1943 | Haack | 260/397.7 |
| 3,242,174 | 3/1966 | McManus et al. | 260/247.1 |
| 4,515,620 | 5/1985 | Bohner | 71/91 |

FOREIGN PATENT DOCUMENTS

| | | | |
|---|---|---|---|
| 0248042 | 2/1961 | Australia | 564/40 |
| 0990860 | 5/1965 | United Kingdom | 564/40 |

OTHER PUBLICATIONS

J. Med. Chem. 8, 766-776 (1965), J. M. McManus et al., "Sulfamylurea Hypoglycemic Agents. I. Synthesis and Screening".

J. Med. Chem. 8, 777-781 (1965), Edward H. Wiseman et al., "Sulfamylurea Hypoglycemic Agents. II. Drug Dynamic Studies".

J. Med. Chem. 8, 781-784 (1965), J. W. McFarland et al, "Sulfamylurea Hypoglycemic Agents. III. Tetrasubstituted Sulfamylureas and N-Sulfamylcarbamates".

Ann. 562, 214 (1949), S. Peterson, "Uber neue Reaktionen von Sulfamiden".

Primary Examiner—Glennon H. Hollrah
Assistant Examiner—Peter O'Sullivan
Attorney, Agent, or Firm—Ruth H. Newtson; Ronald A. Daignault; Michael J. Atkins

[57] ABSTRACT

The present invention provides pharmaceutically useful compounds which are aminosulfonyl urea compounds which are ACAT inhibitors rendering them useful in controlling blood cholesterol levels, pharmaceutical compositions and methods of using the ACAT inhibitors and closely related compounds which are also aminosulfonyl urea compounds.

2 Claims, No Drawings

AMINOSULFONYL UREA ACAT INHIBITORS

CROSS-REFERENCE TO RELATED APPLICATIONS

This application is a continuation-in-part of copending application Ser. No. 07/610,287, filed Nov. 7, 1990, now abandoned.

BACKGROUND OF THE INVENTION

This invention relates to chemical compounds having pharmacological activity, to pharmaceutical compositions which include these compounds, and to a pharmaceutical method of treatment. More particularly, this invention concerns certain novel compounds which inhibit the enzyme acylcoenzyme A: cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which could be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE STATEMENT

U.S. Pat. No. 4,515,620, issued May 7, 1985, describes and claims compounds useful to control plant growth and having the formula

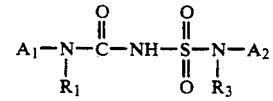

wherein $A_1$ is pyrimidin-2-yl or 1,3,5-triazin-2-yl, each of which is unsubstituted or monosubstituted in the 4 position or disubstituted in the 4- and 6-positions; $A_2$ is phenyl, naphthyl or indanyl, each of which is unsubstituted or substituted; and each of $R_1$ and $R_3$ is independently hydrogen or alkyl having from 1 to 4 carbon atoms. Compounds wherein $A_1$ and $A_2$ are homocyclic or heterocyclic aromatic groups other than those mentioned above are disclosed on a generic basis but there does not appear to be an adequate teaching contained in the patent to render it enabling with respect to this broader disclosure.

U.S. Pat. No. 3,242,174, issued Mar. 22, 1966, Great Britain 990,860, French 2806M, all of which appear to be equivalent, J. Med. Chem. 8(6), 766-776 (1965), J. Med. Chem. 8, 777-781 (1965) and J. Med. Chem. 8, 781-784 (1965) describe compounds useful in lowering blood sugar having the following formulas:

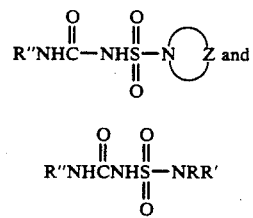

wherein R'' can be a cycloalkyl $C_{4-9}$, alkyl$C_{2-8}$, lower polyfluoroalkyl, aralkyl, pyridylalkyl, thienylalkyl, furylalkyl, morpholinoalkyl, tolyl, p-chlorophenyl, di(-lower alkyl)aminophenyl, and S-(lower alkyl)mercaptophenyl; R is lower alkyl, and R' is lower alkyl, lower alkenyl, phenyl, cycloalkyl$C_{3-8}$, cycloalkenyl, aralkyl, pyridylalkyl, thienylalkyl furylalkyl, and ring substituted derivatives thereof. The

group forms various heterocyclic groups.

Belgian 594,041, Swiss 421,936, and British 896,455 appear to be equivalents and disclose compounds useful in lowering blood sugar having the formula

wherein $R_1$ is a disubstituted amino group, specifically dipropylamino, piperidino, morpholino, pyrrolidino, hexamethyleneamino, and isoquinolino; and $R_2$ is a hydrocarbon radical of aliphatic character which may be substituted by a phenyl or substituted phenyl group, specifically cyclohexyl, n-butyl, ethyl, phenylethyl, —CH(CHMe₂)₂, benzyl, and —CH₂CH(CH₃)₂.

French Patent 993,465 describes the following compound as being useful as a dye or in agriculture:

wherein Ar is phenyl.

Ann. 562, 214 (1949) describes the following compounds:

| | O    O | | |
|---|---|---|---|
| | ‖    ‖ | | |
| | $R_1NHCNHSNR_2R_3$ | | |
| | ‖ | | |
| | O | | |
| $R_1$ | $R_2$ | $R_3$ | |
| $Cl(CH_2)_6—$ | H | H | |
| Phenyl | H | H | |
| $Cl(CH_2)_6—$ | $CH_3$ | $CH_3$ | |
| Phenyl | $CH_3$ | $CH_3$ | |

SUMMARY OF THE INVENTION

The present invention provides a method of using a class of aminosulfonyl urea compounds which have acyl-CoA: cholesterol acyltransferase (ACAT) inhibitory activity rendering them useful in lowering blood cholesterol levels. The compounds of the following structure are useful in treating hypercholesterolemia.

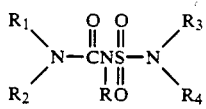   Formula I wherein R is hydrogen, a straight or branched alkyl having from 1 to 8 carbon atoms, or benzyl; wherein each of $R_1$, $R_2$, $R_3$, and $R_4$ is selected from:

(a) hydrogen,
(b) the group

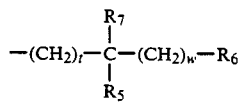

wherein t is zero to 4; w is zero to 4 with the proviso that the sum of t and w is not greater than 5; $R_7$ and $R_5$ are independently selected from hydrogen or alkyl having from 1 to 6 carbon atoms, or when $R_7$ is hydrogen, $R_5$ can be selected from the groups defined for $R_6$; and $R_6$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or $(CH_2)_q$—$NR_9R_8$ wherein $R_9$ and $R_8$ are independently hydrogen or alkyl of from 1 to 4 carbon atoms, and q is zero or one;

(c) a straight or branched hydrocarbon chain having from 1 to 20 carbon atoms and which is saturated or contains from 1 to 3 double bonds;

(d) an alkyl group having from 1 to 6 carbon atoms wherein the terminal carbon is substituted with hydroxy, —$NR_9R_8$ wherein $R_9$ and $R_8$ have the meanings defined above, or —COOalkyl wherein alkyl is straight or branched and has from 1 to 4 carbon atoms;

(e) —$(CH_2)_pQ$ wherein p is a number from zero to 3 and Q is a 5- or 6-membered monocyclic or fused bicyclic heterocycle containing at least 1 to 4 nitrogen, oxygen, or sulfur atoms in at least one ring member;

(f) phenyl or phenyl substituted with from 1 to 3 substituents selected from straight or branched alkyl having from 1 to 6 carbon atoms, alkoxy which is straight or branched and has from 1 to 6 carbon atoms, alkylthio which is straight or branched and has from 1 to 6 carbon atoms, $(CH_2)_q$—$NR_9R_8$ wherein $R_9$ and $R_8$ and q have the meanings defined above, hydroxy, nitro, chlorine, fluorine, bromine, or trifluoromethyl; or (g) $NR_3R_4$ taken together form a monocyclic heterocyclic group selected from pyrrolidino, piperidino, morpholino, or piperazino, each of which is unsubstituted or is substituted with one substituent selected from benzhydryl, straight or branched alkyl having from 1 to 6 carbon atoms, phenyl, benzyl, or substituted phenyl or substituted benzyl wherein the substituents vary from 1 to 3 and can be on any position of 2 through 6 of the aromatic ring and are selected from straight or branched alkyl having from 1 to 4 carbon atoms, straight or branched alkoxy having from 1 to 4 carbon atoms, hydroxy, fluorine, chlorine, bromine, trifluoromethyl, or nitro;

(h) cycloalkyl $C_{3-7}$; or (i) $R_3$ is hydrogen and $R_4$ is 9-fluorenyl; or a pharmaceutically acceptable salt thereof with the proviso that at least one of $R_1$ and $R_2$ and one of $R_3$ and $R_4$ is other than hydrogen and with the proviso that when both of $R_1$ and $R_2$ or when both of $R_3$ and $R_4$ are the group

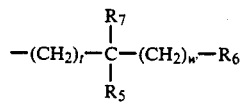

$R_5$ is hydrogen or alkyl.

This invention also provides as novel compounds which are useful in lowering blood cholesterol levels and in treating hypercholesterolemia the compounds of the following Formula II:

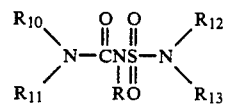   Formula II wherein R is hydrogen, a straight or branched alkyl group having from 1 to 8 carbon atoms or benzyl; wherein each of $R_{10}$, $R_{11}$, $R_{12}$, and $R_{13}$ is selected from
(a) hydrogen,
(b) the group

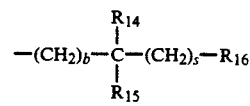

wherein b is zero to 4; s is zero to 4 with the proviso that the sum of b and s is not greater than 5; $R_{14}$ and $R_{15}$ are independently selected from hydrogen or alkyl having from 1 to 6 carbon atoms, or when $R_{14}$ is hydrogen, $R_{15}$ can be selected from the groups defined for $R_{16}$; and $R_{16}$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or $(CH_2)_s$—$NR_{17}R_{18}$ wherein $R_{17}$ and $R_{18}$ are independently hydrogen or alkyl of from 1 to 4 carbon atoms, and s is zero or one;

(c) a straight or branched hydrocarbon chain having from 10 to 20 carbon atoms and which is saturated or contains from 1 to 3 double bonds;

(d) an alkyl group having from 1 to 6 carbon atoms wherein the terminal carbon is substituted with hydroxy, —$NR_{17}R_{18}$ wherein $R_{17}$ and $R_{18}$ have the meanings defined above, or —COOalkyl wherein alkyl is straight or branched and has from 1 to 4 carbon atoms;

(e) phenyl or phenyl substituted with from 1 to 3 substituents selected from straight or branched alkyl having from 1 to 6 carbon atoms, alkoxy which is straight or branched and has from 1 to 6 carbon atoms, alkoxy which is straight or branched and has from 1 to 6 carbon atoms, alkylthio which is straight or branched and has from 1 to 6 carbon atoms, $(CH_2)_s$—$NR_{17}R_{18}$ wherein $R_{17}$ and $R_{18}$ and s have the meanings defined above, hydroxy, nitro, chlorine, fluorine, bromine, or trifluoromethyl;

(f) cycloalkyl $C_{3-7}$; or (g) $R_{12}$ is hydrogen and $R_{13}$ is 9-fluorenyl; or (h) when $R_{10}$ is hydrogen and $R_{11}$ is a straight or branched hydrocarbon chain having from 10 to 20 carbon atoms and which is saturated or contains from 1 to 3 double bonds, or $R_{11}$ is a phenyl group disubstituted in the 2,6-positions, then $NR_{12}R_{13}$ taken together from a monocyclic heterocyclic group selected from pyrrolidino, piperidino, morpholino, or piperazino, each of which is unsubstituted or is substituted with one substituent selected from straight or branched alkyl having from 1 to 6 carbon atoms, phenyl, benzyl, or substituted phenyl or substituted benzyl wherein the substituents vary from 1 to 3 and can be on any position of 2 through 6 of the aromatic ring and are selected from straight or branched alkyl having from 1 to 4 carbon atoms, straight or branched alkoxy having from 1 to 4 carbon atoms, hydroxy, fluorine, chlorine, bromine, trifluoromethyl, or nitro; or a pharmaceutically acceptable salt thereof, with the proviso that at least one of $R_{10}$ and $R_{11}$ and one of $R_{12}$ and $R_{13}$ is other than hydrogen, and with the proviso that when both of $R_{10}$ and $R_{11}$ or when both of $R_{12}$ and $R_{13}$ are the group

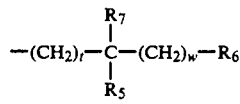

$R_5$ is hydrogen or alkyl.

DETAILED DESCRIPTION OF INVENTION

The compounds of Formulas I and II provide a class of aminosulfonyl ureas which are ACAT inhibitors rendering them useful in treating hypercholesterolemia and atherosclerosis.

Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

The term alkylthio having from 1 to 6 carbon atoms means the group $C_{1-6}alkyl-S-$ wherein the alkyl moiety is straight or branched.

A 5- or 6-membered monocyclic or fused bicyclic heterocycle is a monocyclic or fused bicyclic aromatic ring containing at least 1 to 4 heteroatoms in at least one ring, such as nitrogen, oxygen, or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycle containing a nitrogen atom.

More specifically, such a heterocycle may be a 2- or 3-thienyl; 2- or 3-furanyl; 2-, or 3-, or 4-pyridyl or 2-, or 3-, or 4-pyridyl N-oxide; 2-, 4-, or 5-pyrimidinyl; 3- or 4 pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3- or 5-(1,2,4,-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Preferred embodiments of the novel compounds of this invention as depicted by Formula II include compounds wherein one of $R_{10}$ and $R_{11}$ is hydrogen and the other of $R_{10}$ and $R_{11}$ is phenyl or substituted phenyl. More preferred are compounds wherein one of $R_{10}$ and $R_{11}$ is a disubstituted phenyl and most preferably disubstituted in the 2,6-position. Also preferred are compounds of Formula II wherein one of $R_{12}$ and $R_{13}$ is hydrogen and the other of $R_{12}$ and $R_{13}$ is phenyl or substituted phenyl. The most preferred compounds of Formula II may be depicted by the following general Formula III:

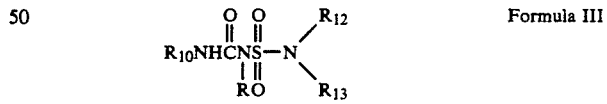

wherein R is hydrogen, a straight or branched alkyl having from 1 to 8 carbon atoms, or benzyl; $R_{10}$ is phenyl or substituted phenyl and $R_{12}$ and $R_{13}$ are hydrogen, phenyl, substituted phenyl or a straight or branched hydrocarbon chain which is saturated or contains from 1 to 3 double bonds.

Pharmaceutically acceptable salts of the compounds of Formula I, II, and III are also included as a part of the present invention.

The base salts may be generated from compounds of Formulas I, II, and III by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, *J Pharm Sciences* 66:1–19 (1977).

Suitable acids for forming acid salts of the compounds of Formulas I, II, and III which contain a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica* 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit the activity of the enzyme by 50%.

TABLE 1

| Example | IAI $IC_{50}$ ($\mu$M) |
|---|---|
| 1 | 0.24 |
| 2 | 4.1 |
| 3 | 16.0 |
| 4 | 0.36 |

TABLE 1-continued

| Example | IAI $IC_{50}$ ($\mu$M) |
|---|---|
| 5 | 30.0 |
| 6 | 11.0 |
| 7 | 5.9 |
| 8 | 3.9 |
| 9 | 2.2 |
| 10 | 25.0 |
| 11 | 0.40 |
| 12 | 1.9 |
| 13 | 10.4 |
| 14 | 0.51 |
| 15 | 55.0 |
| 16 | 8.1 |
| 17 | 1.7 |
| 18 | 2.5 |
| 19 | 3.8 |
| 20 | 1.7 |
| 21 | 0.36 |
| 22 | 0.42 |
| 23 | 0.42 |
| 24 | 2.1 |
| 25 | 0.42 |
| 26 | 0.72 |
| 27 | 69.0 |
| 28 | 1.1 |
| 29 | 0.23 |
| 30 | 2.3 |
| 31 | 1.9 |
| 32 | 18.0 |
| 33 | 2.7 |
| 34 | 1.2 |
| 35 | 0.14 |
| 36 | 0.10 |
| 37 | 0.33 |
| 38 | 15.0 |
| 39 | 17.0 |
| 42 | 16.0 |
| 43 | 0.53 |
| 44 | >5 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. Compounds were dosed at 30 mg/kg unless otherwise noted. The results of this trial for representative compounds of the present invention appear in Table 2.

TABLE 2

| Compound of Example | % Change in Plasma TC Values (mg/dl) |
|---|---|
| 1* | −59 |
| 2* | −14 |
| 3 | −37 |
| 4* | −66 |
| 5 | — |
| 6* | −54 |
| 7* | −20 |
| 8 | — |
| 9* | −59 |
| 10* | −4 |
| 11* | −60 |
| 12* | −41 |
| 13 | −67 |

TABLE 2-continued

| Compound of Example | % Change in Plasma TC Values (mg/dl) |
| --- | --- |
| 14 | −77 |
| 15 | −30 |
| 16 | −19 |
| 17 | −53 |
| 18 | −19 |
| 19 | −59 |
| 20 | −71 |
| 21 | −68 |
| 22 | −76 |
| 23 | −75 |
| 24 | −48 |
| 25 | −60 |
| 26 | −57 |
| 27 | +5 |
| 28 | −60 |
| 29 | −64 |
| 30 | −56 |
| 31 | −60 |
| 32 | −17 |
| 33 | −67 |
| 34 | −70 |
| 35 | −71 |
| 36 | −71 |
| 37 | −65 |
| 38 | −49 |
| 39 | −13 |
| 42 | −44 |
| 43 | −68 |
| 44 | −8 |

*Dosed at 50 mg/kg

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets. Pharmaceutical compositions of the compounds of general Formula I are prepared by procedures well known in the art.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of general Formulas I and II are prepared as generally depicted in Chart I wherein R is as defined in Formulas I and II; $R_{20}$ can be the same as $R_1$ or $R_{10}$; $R_{21}$ can be the same as $R_2$ or $R_{11}$; $R_{22}$ can be the same as $R_3$ or $R_{12}$; and $R_{23}$ can be the same as $R_4$ or $R_{13}$ as generally defined in Formulas I and II.

An amine $(R_{20}R_{21}NH)(1)$ is reacted with N-chlorosulfonyl isocyanate (2) in an inert solvent such as diethyl ether, tetrahydrofuran, hexane, dichloromethane, or ethyl acetate. The reaction temperature is kept between −30° C. and 25° C. under an inert atmosphere such as nitrogen or argon. Reaction times range from 1 hour to 24 hours. The solvent is removed to give the chlorosulfonyl urea intermediate (3), which is then reacted with a second amine $(R_{22}R_{23}NH)$ in an inert solvent such as described above in the presence of an acid scavenger such as triethylamine. Reaction temperatures again range from −30° C. to 25° C. and times range from 1 hour to 24 hours. Removal of the solvents followed by an appropriate purification technique (i.e., recrystallization or chromatography) then gives the compounds (4) of this invention. The aminosulfonyl urea (4) can be converted to its base salt(s) by reacting with an appropriate metal or amine base. The base salt can then be reacted with an appropriate alkylating agent such as R-I wherein R is as defined above only R is other than hydrogen and I is iodine.

The following examples further illustrate the preparation of compounds of Formulas I and II.

EXAMPLE 1

Synthesis of N-[2,6-bis(1-methylethyl)phenyl]-N'-[[bis(11-methylethyl)amino]sulfonyl]urea A solution of [[[2,6-bis(1-methylethyl)phenyl]amino]carbonyl]sulfamoyl chloride (5.0 g, 15.7 mmoles) in 80 mL THF was added dropwise to a solution of diisopropylamine (3.17 g, 31.4 mmoles) in 100 mL THF at 25° C. under an atmosphere of $N_2$. This was stirred for 16 hours and then partitioned between EtOAc and H₂O. The EtOAc layer was dried with MgSO₄, filtered, and concentrated to give a pale yellow oil. Chromatography (SiO₂, 10% EtOAc/hexanes) gave 3.47 g of a clear oil which was triturated with hexanes to give 1.83 g (30%) of the title compound as a white solid, mp 151°–153° C.

EXAMPLE 2

Synthesis of N-[2,6-bis(1-methylethyl)phenyl]-N'-[[(diphenylmethyl)amino]sulfonyl]urea A solution of [[[2,6-bis(1-methylethyl)phenyl]amino]carbonyl]sulfamoyl chloride (1.0 g, 3.1 mmoles) in 60 mL Et₂O was added dropwise to a solution of benzhydrylamine (0.56 g, 3.1 mmoles) and 0.5 mL triethylamine (3.4 mmoles) in 60 mL Et₂O at −15° C. (acetone/ice bath) under an atmosphere of N₂. The resulting suspension was warmed to 25° C. and stirred for 16 hours. This was then partitioned between 1N HCl and EtOAc. The EtOAc layer was dried with MgSO₄, filtered, and evaporated to give an off white solid. Chromatography (SiO₂, 30% EtOAc/hexanes) gave 0.49 g (34%) of the title compound as a white solid, mp 182°–185° C.

EXAMPLE 3

Synthesis of N-2,6-bis(1-methylethyl)phenyl]-N'-[[(diphenylamino)sulfonyl]urea

A solution of diphenylamine (3.0 g, 17.7 mmoles) in 80 mL THF was added dropwise to a suspension of NaH (0.78 g, 60% dispersion in mineral oil, 19.5 mmoles) in 50 mL THF at 0° C. The resulting mixture was warmed to 25° C. and stirred for 16 hours under an atmosphere of N₂. A solution of [[[2,6-bis(1-methylethyl)phenyl]amino]carbonyl]sulfamoyl chloride (2.82 g, 8.8 mmoles) in 50 mL THF was added dropwise to the base containing mixture and the resulting brown suspension was stirred for 16 hours at 25° C. It was then carefully quenched by adding 20 mL 1N HCl and then extracted with EtOAc, the organic layer dried with MgSO₄, filtered, and concentrated to give a green/brown solid. Chromatography (SiO₂, 10% EtOAc/hexanes) gave recovered diphenylamine and 1.88 g of title compound as a tan solid (46%), mp 169°–170° C.

EXAMPLE 4

Synthesis of N-[2,6-bis(1-methylethyl)phenyl]-N'-[[(dibutylamino)sulfonyl]urea

A solution of [[[2,6-bis(1-methylethyl)phenyl]amino]carbonyl]sulfamoyl chloride (25.0 g, 78.4 mmoles) in 250 mL THF was added dropwise to a solution of di-n-butylamine (10.13 g, 78.4 mmoles) and excess triethylamine (~12 mL) in 250 mL THF at 25° C. under an atmosphere of N₂. This was stirred at 25° C. for 16 hours and then concentrated in vacuo to give an oily residue which was partitioned between 1N HCl and EtOAc. The EtOAc layer was dried with MgSO₄, filtered, and evaporated to give a brown oil. Chromatography (SiO₂, 10% EtOAc/hexanes) gave a tan oil which was triturated with hexanes to give 12.21 g (38%) of the title compound as a white solid, mp 98°–101° C.

EXAMPLE 5

Synthesis of N-[[[2,6-bis(1-methylethyl)phenyl]amino]sulfonyl]-N'-(diphenylmethyl)urea A solution of [[(diphenylmethyl)amino]carbonyl]sulfamoyl chloride (1.5 g, 4.6 mmoles) in 50 mL Et₂O was added dropwise to a solution of 2,6-diisopropyl aniline (0.82 g, 4.6 mmoles) and 1.0 mL triethylamine in 50 mL Et₂O at −15° C. under an atmosphere of N₂. This was warmed to 25° C. and stirred for 16 hours and then partitioned between EtOAc and 1N HCl. The organic layer was dried with MgSO₄, filtered, and concentrated to give a pale pink oil. Chromatography (SiO₂, 10% EtOAc/hexanes) gave 0.56 g (26%) of a clear oil which solidified upon standing to give a white solid, mp 92°–95° C.

When in the procedure of Example 4 an appropriate amount of the amine listed below was substituted for di-n-butylamine, the respective product listed below was obtained.

| Example | Amine | Product |
| --- | --- | --- |
| 6 | 2,6-diisopropylaniline | N-[2,6-bis(1-methylethyl)phenyl]-N'-[[[2,6-bis(1-methylethyl)phenyl]amino]sulfonyl]urea, mp 169–172° C. |
| 7 | 2,2-diphenylethylamine | N-[2,6-bis(1-methylethyl)phenyl]-N'-[[(2,2-diphenylethyl)amino]sulfonyl]urea, mp 190–191° C. |
| 8 | dimethylamine | N-[2,6-bis(1-methylethyl)phenyl]-N'-[(dimethylamino)sulfonyl]urea, mp 144–147° C. |
| 9 | bis(phenylmethyl)amine | N-[2,6-bis(1-methylethyl)phenyl]-N'-[(bis(phenylmethyl)amino)sulfonyl]urea, dmp 224–227° C. |
| 10 | 9-fluorenylamine | N-[2,6-bis(1-methylethyl)phenyl]-N'-[(9H-fluoren-9-ylamino)sulfonyl]urea, mp 224–227° C. |
| 11 | N-isopropyl-N-phenylmethylamine | N-[2,6-bis(1-methylethyl)phenyl]-N'-[[(1-methylethyl)(phenylmethyl)amino]sulfonyl]urea, mp 142–144° C. |
| 12 | dioctylamine | N-[2,6-bis(1-methylethyl)phenyl]-N'-[(dioctylamino)sulfonyl]urea, mp 70–72° C. |
| 13 | 4-phenylpiperidine | N-[2,6-bis(1-methylethyl)phenyl]-N'-[(4-phenyl-1-piperidinyl)sulfonyl]urea, mp 154–159° C. |
| 14 | dihexylamine | N-[2,6-bis(1-methylethyl)phenyl]-N'-[(dihexylamino)sulfonyl]urea, mp 70–73° C. |
| 15 | bis[3-(dimethylamino)propyl]amine | N-[[bis[3-(dimethylamino)propyl]amino]sulfonyl]-N'-[2,6-bis(1-methylethyl)phenyl]urea, ¹H NMR (CDCl₃) δ 8.18(s, 1H), 7.28–7.10 (m, 4H), 3.33–3.21(m, 6H), 2.65(t, 4H), 2.41(s, 12H), 1.85(t, 4H), 1.18 (d, 12H) ppm |
| 16 | hexylamine | N-[2,6-bis(1-methylethyl)phenyl]-N'-[(hexylamino)sulfonyl]urea, mp 161–162° C. |
| 17 | bis[(tetrahydro-2-furanyl)methyl]amine | N-[2,6-bis(1-methylethyl)phenyl]-N'-[[bis[(tetrahydro-2-furanyl)methyl]amino]sulfonyl]urea, ¹H NMR (CDCl₃) δ 8.50(bs, 1H), 8.01(bs, 1H), 7.32–7.17(m, 3H), 4.26–4.23(m, |

-continued

| Example | Amine | Product |
|---|---|---|
| | | 2H), 3.98-3.82(m, 4H), 3.66-3.38(m, 4H), 3.20-3.09(m, 2H), 2.09-1.89(m, 6H), 1.66-1.29(m, 2H), 1.22(d, 12H) ppm |
| 18 | diethylamine | N-[2,6-bis(1-methylethyl)-phenyl]-N'-[(diethylamino)-sulfonyl]urea, mp 139-142° C. |
| 19 | N-methyl-N-octylamine | N-[2,6-bis(1-methylethyl)-phenyl]-N'-[(methyloctyl amino)sulfonyl]urea, $^1$H NMR (CDCl$_3$) δ 7.73(bs, 1H), 7.37-7.06(m, 4H), 3.29-3.02(m, 4H), 2.92(s, 3H), 1.60(m, 4H), 1.29-1.12(m, 22H), 0.94-0.88(t, 3H) ppm |
| 20 | N-methyl-N-(2-phenylethyl)-amine | N-[2,6-bis(1-methylethyl)-phenyl]-N'-[[methyl(2-phenylethyl)amino]-sulfonyl]urea, mp 162-164° C. |
| 21 | N-cyclohexyl-N-isopropyl-amine | N-[2,6-bis(1-methylethyl)-phenyl]-N'-[[cyclohexyl(1-methylethyl)amino]sulfonyl] urea, mp 162-164° C. |
| 22 | dipentylamine | N-[2,6-bis(1-methylethyl)-phenyl]-N'-[(dipentyl-amino)sulfonyl]urea, mp 93-95° C. |
| 23 | bis(2-methyl-propyl)amine | N-[2,6-bis(1-methylethyl)-phenyl]-N'-[[bis(2-methyl-propyl)amino]sulfonyl]urea, mp 122-125° C. |
| 24 | N-ethyl-N-(2-propenyl)amine | N-[2,6-bis(1-methylethyl)-phenyl]-N'-[[ethyl(2-propenyl)amino]sulfonyl]-urea, mp 124-128° C. |
| 25 | bis(3-methyl-butyl)amine | N-[[bis(3-methylbutyl)-amino]sulfonyl]-N'-[2,6-bis(1-methylethyl)-phenyl]urea, mp 106-110° C. |
| 26 | didecylamine | N-[2,6-bis(1-methylethyl)-phenyl]-N'-[(didecylamino)-sulfonyl]urea, mp 35-37° C. |
| 27 | didodecylamine | N-[2,6-bis(1-methylethyl)-phenyl]-N'-[(didodecyl-amino)sulfonyl]urea, $^1$H NMR (CDCl$_3$) δ 7.92(bs, 1H), 7.77(bs, 1H), 7.26-7.15(m, 3H), 3.28-3.10(m, 6H), 1.58(m, 4H), 1.43-1.13(m, 48H), 0.91-0.85 (t, 6H) ppm |
| 28 | diisopropyl amine | N-[2,6-bis(1-methylethyl)-phenyl]-N'-[(diisopropyl-amino)sulfonyl]urea, mp 119-121° C. |
| 29 | dicyclohexyl-amine | N-[2,6-bis(1-methylethyl)-phenyl]-N'-[(dicyclohexyl-amino)sulfonyl]urea, mp 163-165° C. |
| 30 | N-methyl-N-butylamine | N-[2,6-bis(1-methylethyl)-phenyl]-N'-[(butylmethyl-amino)sulfonyl]urea, mp 109-110° C. |
| 31 | N-methyl-N-octadecylamine | N-[2,6-bis(1-methylethyl)-phenyl]-N'-[(methylocta-decylamino)sulfonyl]urea, mp 56-59° C. |
| 32 | isopropylamine | N-[2,6-bis(1-methylethyl)-phenyl]-N'-[[(1-methyl-ethyl)amino]sulfonyl]urea, mp 177-179° C. |
| 33 | di-2-propenyl-amine | N-[2,6-bis(1-methylethyl)-phenyl]-N'-[(di-2-propenyl-amino)sulfonyl]urea, mp 142-145° C. |
| 34 | N-ethyl-N-butylamine | N-[2,6-bis(1-methylethyl)-phenyl]-N'- (butylethyl-amino)sulfonyl]urea, mp 101-104° C. |
| 35 | N-tert-butyl- | N-[2,6-bis(1-methylethyl)- |

-continued

| Example | Amine | Product |
|---|---|---|
| | N-isopropyl-amine | phenyl]-N'-[[(1,1-dimethyl-ethyl)(1-methylethyl)-amino]sulfonyl]urea, mp 146-147° C. |
| 36 | bis(1-methyl-propyl)amine | N-[2,6-bis(1-methylethyl)-phenyl]-N'-[[bis(1-methyl-propyl)amino]sulfonyl]urea, mp 144-146° C. |
| 37 | N-methyl-N-tetradecyl-amine | N-[2,6-bis(1-methylethyl)-phenyl]-N'-[(methyltetra-decylamino)sulfonyl]urea, mp 49-52° C. |
| 38 | pyrrolidine | Urea, N-[2,6-bis(1-methyl-ethyl)phenyl]-N'-(1-pyrrolidinylsulfonyl); $^1$H NMR (DMSO D$_6$) δ 10.2(bs, 1H), 7.7(bs, 1H), 7.3(t, 1H), 7.1(d, 2H), 3.4(bs, 4H), 3.1(m, 2H), 1.8(bs, 4H), 1.2(d, 12H) ppm |
| 39 | Piperidine | Urea, N-[2,6-bis(1-methyl-ethyl)phenyl]-N'-(1-piperidinylsulfonyl); $^1$H NMR (CDCl$_3$) δ 8.3(bs, 1H), 7.8(bs, 1H), 2.1(m, 3H), 3.3(t, 4H), 3.0(m, 2H), 1.7(m, 4H), 1.6(m, 2H), 1.2(d, 12H) ppm |

EXAMPLE 40

Synthesis of [[[2,6-bis(1-methylethyl)phenyl]amino]carbonyl]sulfamoyl chloride

A solution of 2,6-diisopropylaniline (30.0 g, 0.169 moles in 150 mL Et$_2$O was added dropwise to a solution of N-chlorosulfonyl isocyanate (14.73 mL, 0.169 moles) in 100 mL Et$_2$O at −15° C. (acetone/ice bath) under an atmosphere of N$_2$. The resulting off-white suspension was stirred at −15° C. for 1 hour and the solid was collected by vacuum filtration. The solid was washed with hexanes and air dried to give 53.79 g (99%) of the title compound as a white solid, mp 130°-134° C.

EXAMPLE 41

Synthesis of [[(diphenylmethyl)amino]carbonyl]sulfamoyl chloride

A solution of benzhydrylamine (4.0 g, 21.8 mmoles) in 50 mL Et$_2$O was added dropwise to a solution of N-chlorosulfonyl isocyanate (1.90 mL, 21.8 mmoles) in 100 mL Et$_2$O at 15° C. under an atmosphere of N$_2$. Upon addition, the mixture turned cloudy but cleared up after one-half hour of stirring. The reaction mixture was concentrated in vacuo to give a pale yellow solid. Trituration with hexanes gave 6.64 g (94%) of the title compound, mp 80°-88° C.

EXAMPLE 42

Synthesis of N'-[[[2,6-bis(1-methylethyl)phenyl]amino]sulfonyl]N,N-bis(phenylmethyl) urea A solution of dibenzylamine (5.0 g, 25.3 mmol) in 75 mL tetrahydrofuran was added dropwise to a solution of chlorosulfonyl isocyanate (2.21 mL, 25.3 mmol) in 75 mL tetrahydrofuran at 0° C. under an atmosphere of nitrogen. The resulting mixture was warmed to room temperature and stirred for 16 hours. A solution of 2,6-diisopropyl aniline (4.08 g, 23 mmol) and triethyl-amine (3.5 mL, 25 mmol) in 50 mL tetrahydrofuran was added dropwise and the resulting suspension was stirred for 72 hours. Partitioned between 1N HCl and ethyl acetate. The organic layer was dried with MgSO₄, filtered, and evaporated to give an orange oil. Chromatography gave the title compound as a white solid, mp 140°-142° C.

EXAMPLE 43

Synthesis of N-[2,6-bis(1-methylethyl)phenyl]-N'-[(dibutylamino)-sulfonyl]urea, monosodium salt A solution of N-[2,6-bis(1-methylethyl)phenyl]-N'-[(dibutylamino)sulfonyl]urea (15.0 g, 36.4 mmol) in 150 mL tetrahydrofuran was added dropwise to a hexane-washed suspension of sodium hydride (1.53 g, 60% dispersion in mineral oil, 38.3 mmol) in 50 mL tetrahydrofuran at 0° C. under an atmosphere of nitrogen. The resulting solution was warmed to room temperature and stirred for 16 hours. The reaction was concentrated and the residue was triturated with ether and filtered to remove inorganic impurities. The filtrate was evaporated to give a solid, triturated with hexane to give the title compound, mp 217°-219° C.

EXAMPLE 44

N'-2,6-bis(1-methylethyl)phenyl]N-methyl-(dibutylamino)sulfonyl]urea 1,8-Diazabicyclo[5.4.0]undec-7-ene (1.6 mL, 10.7 mmol) was added dropwise to a solution of N-[2,6-bis(1-methylethyl)phenyl]-N'-[(dibutylamino)sulfonyl]urea (4.0 g, 9.7 mmol) and methyl iodide (1.52 g, 10.7 mmol) in 100 mL acetonitrile at −15° C. The resulting mixture was warmed to room temperature and stirred for 16 hours. Concentrated in vacuo and partitioned between 1N HCl and ethyl acetate. The organic layer was dried with MgSO₄, filtered, and concentrated to give an orange oil. Chromatography gave the title compound as a clear oil; ¹H NMR (DMSO-d₆) δ 8.57 (s, 1H), 7.31–7.15 (m, 3H), 3.33–3.21 (m, 7H), 3.05 (heptet, 2H), 1.57–1.46 (m, 4H), 1.35–1.20 (m, 4H), 1.13 (d, 12H), 0.990 (t, 6H).

CHART I

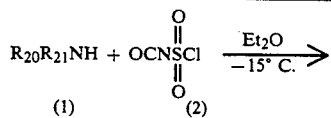

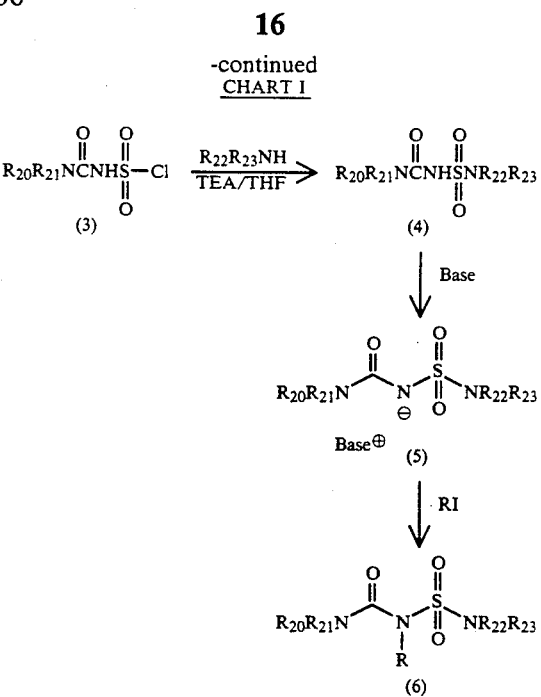

We claim:

1. A compound of the formula

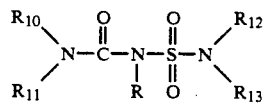

wherein R is hydrogen, straight or branched alkyl having from 1 to 8 carbon atoms, or benzyl;
wherein $R_{10}$ is hydrogen;
wherein $R_{11}$ is 2,6-bis(1-methylethyl)phenyl;
wherein each of $R_{12}$ and $R_{13}$ is a straight or branched hydrocarbon chain having from 10 to 20 carbon atoms and which is saturated or contains from 1 to 3 double bonds, or cycloalkyl having from 3 to 7 carbon atoms; or a pharmaceutically acceptable salt thereof.

2. A compound of claim 1 which is
N-[2,6-bis(1-methylethyl)phenyl]-N'-[(didecylamino)-sulfonyl]urea,
N-[2,6-bis(1-methylethyl)phenyl]-N'-[(didodecylamino)sulfonyl]urea, and
N-[2,6-bis(1-methylethyl)phenyl]-N'-[(dicyclohexylamino)sulfonyl]urea.

* * * * *